(12) United States Patent
Falcó et al.

(10) Patent No.: US 7,943,611 B2
(45) Date of Patent: May 17, 2011

(54) IMIDAZO[1,2-A]PYRIDIN-3-YL-ACETIC ACID HYDRAZIDES, PROCESSES, FOR THEIR PREPARATION AND PHARMACEUTICAL USES THEREOF

(75) Inventors: José Luís Falcó, Barcelona (ES); Albert Palomer, Barcelona (ES); Antonio Guglietta, Barcelona (ES)

(73) Assignee: Ferrer International, S.A., Barcelona (ES)

( * ) Notice: Subject to any disclaimer, the term of this patent is extended or adjusted under 35 U.S.C. 154(b) by 338 days.

(21) Appl. No.: 12/087,423

(22) PCT Filed: Dec. 21, 2006

(86) PCT No.: PCT/EP2006/070130
§ 371 (c)(1),
(2), (4) Date: Nov. 24, 2008

(87) PCT Pub. No.: WO2007/077159
PCT Pub. Date: Jul. 12, 2007

(65) Prior Publication Data
US 2009/0176777 A1    Jul. 9, 2009

(30) Foreign Application Priority Data

Jan. 3, 2006  (EP) .................................. 06100030

(51) Int. Cl.
*A61K 31/437* (2006.01)
*C07D 471/04* (2006.01)
*C07D 413/12* (2006.01)
*A61K 31/5377* (2006.01)
*A61P 21/00* (2006.01)
*A61P 25/00* (2006.01)

(52) U.S. Cl. .................... 514/233.2; 514/300; 546/121; 544/127

(58) Field of Classification Search ................ 514/233.2, 514/300; 546/121; 544/127
See application file for complete search history.

(56) References Cited

U.S. PATENT DOCUMENTS
4,382,938 A * 5/1983 Kaplan et al. ................. 514/393

FOREIGN PATENT DOCUMENTS
EP        1 104 765 A      6/2001
WO    WO-2005/044818 A2    5/2005

OTHER PUBLICATIONS

Trapani G et al., Journal of Medicinal Chemistry, American Society, vol. 40, 1997, pp. 3109-3118.

* cited by examiner

*Primary Examiner* — Janet L Andres
*Assistant Examiner* — Niloofar Rahmani
(74) *Attorney, Agent, or Firm* — Birch, Stewart, Kolasch & Birch, LLP

(57) ABSTRACT

The invention provides novel imidazo[1,2-a]pyridin-3-yl-acetic acid hydrazides of formula (I) wherein $R_1$, $R_2$ and $R_3$ have different meanings, and pharmaceutically acceptable salts, polymorphs, hydrates, tautomers, solvates and stereoisomers thereof. Compounds of formula (I) are useful for treating or preventing, in a human or non-human mammal, diseases associated with $GABA_A$ receptors modulation, anxiety, epilepsy, sleep disorders including insomnia, and for inducing sedation-hypnosis, anesthesia, sleep and muscle relaxation. The invention also provides synthetic processes for preparing said compounds.

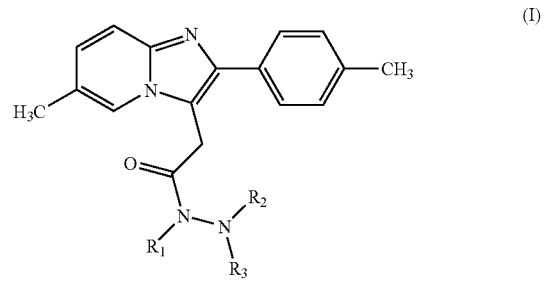

(I)

10 Claims, No Drawings

IMIDAZO[1,2-A]PYRIDIN-3-YL-ACETIC ACID HYDRAZIDES, PROCESSES, FOR THEIR PREPARATION AND PHARMACEUTICAL USES THEREOF

TECHNICAL FIELD

This invention is directed to agents with affinity for $GABA_A$ receptor, specifically to imidazo[1,2-a]pyridin-3-yl-acetic acid hydrazides, and more specifically to (6-methyl-2-p-tolyl-imidazo[1,2-a]pyridin-3-yl)-acetic acid hydrazides.

BACKGROUND OF THE INVENTION $GABA_A$ receptor (γ-aminobutyric acid$_A$) is a pentameric protein which forms a membrane ion channel. $GABA_A$ receptor is implicated in the regulation of sedation, anxiety, muscle tone, epileptogenic activity and memory functions. These actions are due to defined subunits of $GABA_A$ receptor, particularly the $\alpha_1$-and $\alpha_2$-subunits.

Sedation is modulated by the $\alpha_1$-subunit. Zolpidem is characterized by a high affinity for the $\alpha_1$-receptors and its sedative and hypnotic action is mediated by these receptors in vivo. Similarly, the hypnotic action of zaleplon is also mediated by the $\alpha_1$-receptors.

The anxiolytic action of diazepam is mediated by the enhancement of GABAergic transmission in a population of neurons expressing the $\alpha_2$-receptors. This indicates that the $\alpha_2$-receptors are highly specific targets for the treatment of anxiety.

Muscle relaxation in diazepam is mainly mediated by $\alpha_2$-receptors, since these receptors exhibit a highly specific expression in spinal cord.

The anticonvulsant effect of diazepam is partly due to $\alpha_1$-receptors. In diazepam, a memory-impairing compound, anterograde amnesia is mediated by $\alpha_1$-receptors.

$GABA_A$ receptor and its $\alpha_1$-and $\alpha_2$-subunits have been widely reviewed by H. M öhler et al. (J. Pharmacol. Exp. Ther., 300, 2-8, 2002); H. M öhler et al. (Curr. Opin. Pharmacol., 1, 22-25, 2001); U. Rudolph et al. (Nature, 401, 796-800, 1999); and D. J. Nutt et al. (Br. J. Psychiatry, 179, 390-396, 2001).

Diazepam and other classical benzodiazepines are extensively used as anxiolytic agents, hypnotic agents, anticonvulsants and muscle relaxants. Their side effects include anterograde amnesia, decrease in motor activity and potentiation of ethanol effects.

Insomnia is a highly prevalent disease. Its chronicity affects 10% of the population and 30% when transitory insomnia is computed as well. Insomnia describes the trouble in getting to sleep or staying asleep and is associated with next-day hangover effects such as weariness, lack of energy, low concentration and irritability. The social and health impact of this complaint is important and results in evident socioeconomic repercussions.

Pharmacological therapy in the management of insomnia firstly included barbiturates and chloral hydrate, but these drugs elicit numerous known adverse effects, for example, overdose toxicity, metabolic induction, and enhanced dependence and tolerance. In addition, they affect the architecture of sleep by decreasing above all the duration and the number of REM sleep stages. Later, benzodiazepines meant an important therapeutic advance because of their lower toxicity, but they still showed serious problems of dependence, muscle relaxation, amnesia and rebound insomnia following discontinuation of medication.

The latest known therapeutic approach has been the introduction of non-benzodiazepine hypnotics, such as pyrrolo[3,4-b]pyrazines (zopiclone), imidazo[1,2-a]pyridines (zolpidem) and, finally, pyrazolo[1,5-a]pyrimidines (zaleplon). Later, two new pyrazolo[1,5-a]pyrimidines, indiplon and ocinaplon, have entered into development, the latter with rather anxiolytic action. All these compounds show a rapid sleep induction and have less next-day hangover effects, lower potential for abuse and lower risk of rebound insomnia than benzodiazepines. The mechanism of action of these compounds is the alosteric activation of $GABA_A$ receptor through its binding to benzodiazepine binding site (C. F. P. George, The Lancet, 358, 1623-1626, 2001). While benzodiazepines are unspecific ligands at $GABA_A$ receptor binding site, zolpidem and zaleplon show a greater selectivity for $\alpha_1$-subunit. Notwithstanding that, these drugs still affect the architecture of sleep and may induce dependence in long-term treatments.

Research for new active compounds in the management of insomnia answers an underlying health need, because even recently introduced hypnotics still affect the architecture of sleep and may induce dependence in long-term treatments.

It is therefore desirable to focus on the development of new hypnotic agents with a lower risk of side effects.

SUMMARY OF THE INVENTION

The present invention is directed to new imidazo[1,2-a]pyridin-3-yl-acetic acid hydrazides which are active versus $GABA_A$ and, particularly, versus its $\alpha_1$-and $\alpha_2$-subunits. Consequently, the compounds of this invention are useful in the treatment and prevention of all those diseases mediated by $GABA_A$ receptor $\alpha_1$-and $\alpha_2$-subunits. Non-limitative examples of such diseases are sleep disorders, preferably insomnia, anxiety and epilepsy. Non-limitative examples of the relevant indications of the compounds of this invention are all those diseases or conditions, such as insomnia or anesthesia, in which an induction of sleep, an induction of sedation or an induction of muscle relaxation are needed.

Some compounds of the present invention are structurally related to, but patentably distinct from the compound N,N,6-trimethyl-2-p-tolylimidazo[1,2-a]pyridine-3-acetamide, zolpidem, which is described in U.S. Pat. No. 4,382,938, because of their improved properties as shown in the section "Detailed Description of the Invention".

Thus, the present invention describes a novel class of compounds represented by formula (I):

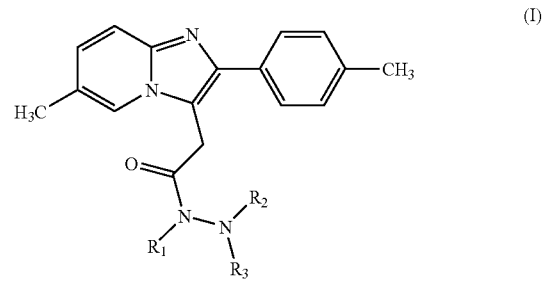

and pharmaceutically acceptable salts, polymorphs, hydrates, tautomers, solvates, and stereoisomers thereof, wherein $R_1$, $R_2$ and $R_3$ are defined below, which are ligands of $GABA_A$ receptor.

It is another object of this invention to provide synthetic processes for preparing the compounds of formula (I) or pharmaceutically acceptable salts thereof.

It also forms part of the invention the use of the compounds of formula (I) or pharmaceutically acceptable salts thereof, for the preparation of a medicament for treating or preventing diseases associated with GABA$_A$ receptor modulation such as anxiety, epilepsy and sleep disorders including insomnia, and for inducing sedation-hypnosis, anesthesia, sleep and muscle relaxation.

DETAILED DESCRIPTION OF THE INVENTION

The present invention relates to novel (6-methyl-2-p-tolyl-imidazo[1,2-a]pyridin-3-yl)-acetic acid hydrazide compounds of formula (I):

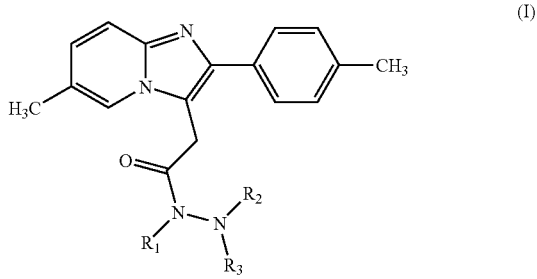

(I)

wherein

R$_1$ is selected from the group consisting of hydrogen, linear or branched alkyl(C$_1$-C$_6$), alkenyl(C$_2$-C$_6$), alkynyl(C$_2$-C$_6$) and cycloalkyl(C$_3$-C$_6$);

R$_2$ and R$_3$ are independently selected from the group consisting of hydrogen, linear or branched alkyl(C$_1$-C$_6$), alkenyl (C$_2$-C$_6$), alkynyl(C$_2$-C$_6$), cycloalkyl(C$_3$-C$_6$) and R$_4$CO, or both R$_2$ and R$_3$ can form, together with the nitrogen atom to which they are attached, a 5-6 membered heterocyclic ring optionally substituted, or a NCR$_5$R$_6$ group;

R$_4$ is selected from the group consisting of linear or branched alkyl(C$_1$-C$_6$), cycloalkyl(C$_3$-C$_6$), aryl optionally substituted and heteroaryl optionally substituted;

R$_5$ is selected from the group consisting of hydrogen, linear or branched alkyl(C$_1$-C$_6$), cycloalkyl(C$_3$-C$_6$) and aryl optionally substituted;

R$_6$ is selected from the group consisting of linear or branched alkyl(C$_1$-C$_6$), cycloalkyl(C$_3$-C$_6$) and aryl optionally substituted;

or both R$_5$ and R$_6$ can form, together with the carbon atom to which they are attached, a 5-6 membered ring optionally substituted;

and pharmaceutically acceptable salts, polymorphs, hydrates, tautomers, solvates, and stereoisomers thereof.

Preferably R$_1$ is selected from the group consisting of hydrogen and methyl; and R$_2$ and R$_3$ are independently selected from the group consisting of hydrogen, acetyl and 2-thiophenecarbonyl, or both R$_2$ and R$_3$ form, together with the nitrogen atom to which they are attached, a heterocycle selected from 1-morpholinyl and 1,2,4-triazin-4-yl, or a NCR$_5$R$_6$ group selected from ethylideneamino, isopropylideneamino and 4-chlorobenzylideneamino.

The term "pharmaceutically acceptable salt" used herein encompasses any salt formed from organic and inorganic acids, such as hydrobromic, hydrochloric, phosphoric, nitric, sulfuric, acetic, adipic, aspartic, benzenesulfonic, benzoic, citric, ethanesulfonic, formic, fumaric, glutamic, lactic, maleic, malic, malonic, mandelic, methanesulfonic, 1,5-naphthalendisulfonic, oxalic, pivalic, propionic, p-toluenesulfonic, succinic, tartaric acids and the like.

The present invention comprises the compounds:

Thiophene-2-carboxylic acid N'-[2-(6-methyl-2-p-tolyl-imidazo[1,2-a]pyridin-3-yl)-acetyl]-hydrazide;

(6-Methyl-2-p-tolyl-imidazo[1,2-a]pyridin-3-yl)-acetic acid N'-acetyl-hydrazide;

(6-Methyl-2-p-tolyl-imidazo[1,2-a]pyridin-3-yl)-acetic acid hydrazide;

2-(6-Methyl-2-p-tolyl-imidazo[1,2-a]pyridin-3-yl)-N-morpholin-4-yl-acetamide;

2-(6-Methyl-2-p-tolyl-imidazo[1,2-a]pyridin-3-yl)-N-[1,2,4]triazol-4-yl-acetamide;

(6-Methyl-2-p-tolyl-imidazo[1,2-a]pyridin-3-yl)-acetic acid N-methyl-hydrazide;

(6-Methyl-2-p-tolyl-imidazo[1,2-a]pyridin-3-yl)-acetic acid (4-chlorobenzylidene)-hydrazide;

(6-Methyl-2-p-tolyl-imidazo[1,2-a]pyridin-3-yl)-acetic acid ethylidene-hydrazide; and (6-Methyl-2-p-tolyl-imidazo[1,2-a]pyridin-3-yl)-acetic acid isopropylidene-hydrazide.

Another aspect of the present invention is to provide a process for preparing the compounds of formula (I) and their pharmaceutically acceptable salts.

The compounds of general formula (I) may be prepared according to the reaction shown in Scheme 1.

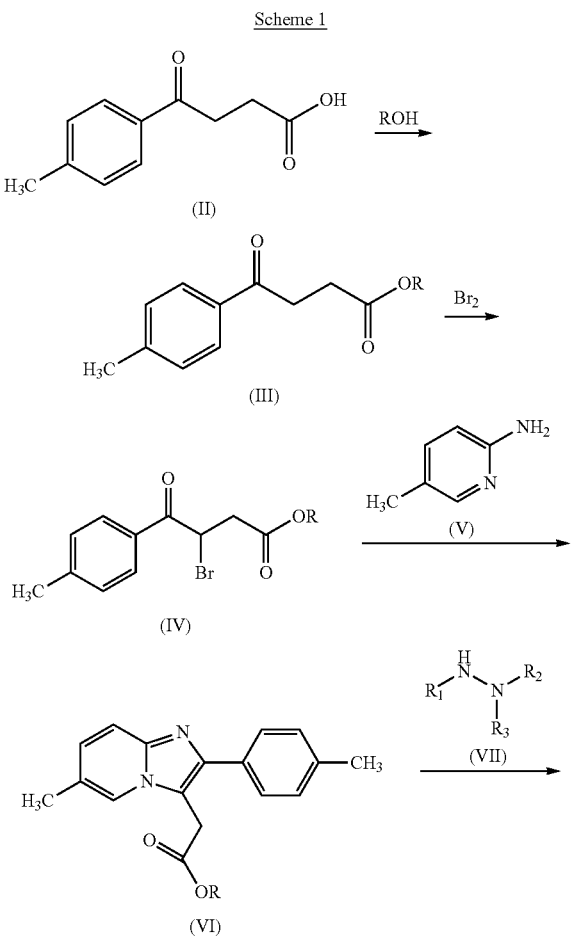

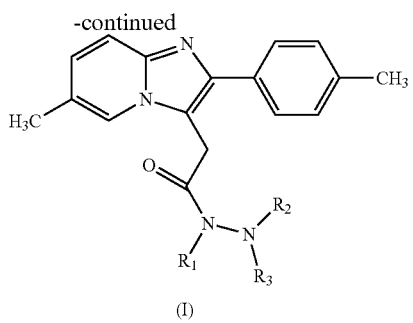

A Fischer esterification of ketoacid (II) was carried out with an alcohol ROH to afford the corresponding ester (III). This ester was brominated in acetic acid at room temperature to yield the bromoketoester (IV). A cyclization with 2-amino-5-methylpyridine (V) afforded the imidazo[1,2-a]pyridin-3-yl-acetic acid ester (VI). Finally, acylic substitution by using a substituted hydrazine (VII) in a suitable solvent at reflux yielded the corresponding final imidazo[1,2-a]pyridin-3-yl-acetic acid hydrazide (I). Suitable solvents to be used in this reaction are selected preferably from linear or branched alkanols ($C_1$-$C_6$), more preferably methanol, or mixtures thereof.

In the case of the N'-acyl hydrazides (I, $R_2$=$R_4$CO), a final step is needed, consisting of reacting (I, $R_2$=H) with the corresponding acid chloride $R_4$COCl in a suitable solvent at room temperature. Suitable solvents to be used in this reaction are selected preferably from halogenated alkanes, more preferably dichloromethane. The reaction occurs conveniently in the presence of a basic compound. Non-limitative basic compounds are alkaline or alkaline earth metal carbonates or acid carbonates, or alkyl-, dialkyl- or trialkylamines, specifically triethylamine, or mixtures thereof, and the like.

In the case of the alkyl-(or aryl-)iden hydrazides (I, $NR_2R_3$=$NCR_5R_6$), a final step is needed, consisting of reacting (I, $R_2$=$R_3$=H) with the corresponding aldehyde or ketone, $R_5COR_6$, in a suitable solvent at room temperature. Suitable solvents to be used in this reaction are selected preferably from linear or branched alkanols ($C_1$-$C_6$), more preferably methanol, or mixtures thereof.

Another aspect of the present invention is to provide the use of a compound of formula (I) for the preparation of a medicament for treating or preventing anxiety in a human or non-human mammal.

Another aspect of the present invention is to provide the use of a compound of formula (I) for the preparation of a medicament for treating or preventing epilepsy in a human or non-human mammal.

Another aspect of the present invention is to provide the use of a compound of formula (I) for the preparation of a medicament for treating or preventing sleep disorders in a human or non-human mammal.

Another aspect of the present invention is to provide the use of a compound of formula (I) for the preparation of a medicament for treating or preventing insomnia in a human or non-human mammal.

Another aspect of the present invention is to provide the use of a compound of formula (I) for the preparation of a medicament for inducing sedation-hypnosis in a human or non-human mammal.

Another aspect of the present invention is to provide the use of a compound of formula (I) for the preparation of a medicament for inducing anesthesia in a human or non-human mammal.

Another aspect of the present invention is to provide the use of a compound of formula (I) for the preparation of a medicament for modulating the necessary time to induce sleep and its duration in a human or non-human mammal.

Another aspect of the present invention is to provide the use of a compound of formula (I) for the preparation of a medicament for inducing muscle relaxation in a human or non-human mammal.

The present invention also relates to a method of treatment or prevention of a human or non-human mammal suffering from diseases associated with $GABA_A$ receptor modulation, which comprises administering to said human or non-human mammal in need thereof a therapeutically effective amount of a compound of formula (I) or a pharmaceutically acceptable salt, polymorph, hydrate, tautomer, solvate or stereoisomer thereof, together with pharmaceutically acceptable diluents or carriers. More specifically, diseases associated with $GABA_A$ receptor modulation comprise diseases associated with $\alpha_1$-$GABA_A$ receptor modulation and/or $\alpha_2$-$GABA_A$ receptor modulation. A non-limitative list of such diseases comprises anxiety, epilepsy, sleep disorders, including insomnia, and the like.

Another aspect of the present invention is to provide a pharmaceutical composition containing a compound of formula (I) or a pharmaceutically acceptable salt, polymorph, hydrate, tautomer, solvate or stereoisomer thereof in association with therapeutically inert carriers.

The compositions include those suitable for oral, rectal and parenteral (including subcutaneous, intramuscular, and intravenous) administration, although the most suitable route will depend on the nature and severity of the condition being treated. The most preferred route of the present invention is the oral route. The compositions may be conveniently presented in unit dosage form, and prepared by any of the methods well known in the art of pharmacy.

The active compound can be combined with a pharmaceutical carrier according to conventional pharmaceutical compounding techniques. The carrier may take a wide variety of forms depending on the form of the preparation desired for administration, e.g. oral or parenteral (including intravenous injections or infusions). On preparing the compositions for oral dosage form, any of the usual pharmaceutical media may be employed. Usual pharmaceutical media include, for example, water, glycols, oils, alcohols, flavoring agents, preservatives, coloring agents, and the like in the case of oral liquid preparations (such as for example, suspensions, solutions, emulsions and elixirs); aerosols; or carriers such as starches, sugars, microcrystalline cellulose, diluents, granulating agents, lubricants, binders, disintegrating agents and the like in the case of oral solid preparations (such as for example, powders, capsules, and tablets); the oral solid preparations being preferred rather than the oral liquid preparations.

Because of their ease of administration, tablets and capsules represent the most advantageous oral dosage unit form, in which case solid pharmaceutical carriers are employed. If desired, tablets may be coated by standard aqueous or non-aqueous techniques.

A suitable dosage range for use is from about 0.01 mg to about 100.00 mg total daily dose, given as a once daily administration or in divided doses if required.

The compounds of the present invention have a high affinity for $\alpha_1$- and $\alpha_2$-$GABA_A$ receptors. These in vitro results are consistent with those in vivo results obtained in sedation-hypnosis tests.

In accordance with the results obtained, certain compounds of the present invention have evidenced pharmacological activity both in vitro and in vivo, which has been similar to or higher than that of prior-art compound zolpidem. All these results support their use in diseases or conditions modulated by $\alpha_1$- and $\alpha_2$-GABA$_A$ receptors, such as insomnia or anesthesia, in which an induction of sleep, an induction of sedation or an induction of muscle relaxation are needed.

The pharmacological activity of the compounds of the present invention has been determined as shown below.

a) Ligand-Binding Assays. Determination of the Affinity of Test Compounds for $\alpha_1$- and $\alpha_2$-GABA$_A$ Receptor Male Sprague-Dawley rats weighing 200-250 g at the time of experiment were used. After decapitation of the animal, the cerebellum (tissue that mostly contains $\alpha_1$-GABA$_A$ receptor) and spinal cord (tissue that mostly contains $\alpha_2$-GABA$_A$ receptor) were removed. The membranes were prepared according to the method by J. Lameh et al. (Prog. Neuro-Psychopharmacol. Biol. Psychiatry, 24, 979-991, 2000) and H. Noguchi et al. (Eur J Pharm, 434, 21-28, 2002) with slight modifications. Once the tissues weighed, they were suspended in 50 mM Tris.HCl (pH 7.4), 1:40 (v/v), or sucrose 0.32 M in the case of spinal cord, homogenized and then centrifuged at 20,000 g for 10 min at 7° C. The resulting pellet was resuspended under the same conditions and centrifuged again. The pellet was finally resuspended on a minimum volume and kept at −80° C. overnight. On the next day, the process was repeated until the final pellet was resuspended at a ratio of 1:10 (v/v) in the case of cerebellum and at a ratio of 1:5 (v/v) in the case of spinal cord.

Affinity was determined by competitive tests using radio-labeled flumazenil as ligand. The tests were performed according to the methods described by S. Arbilla et al. (Eur. J. Pharmacol., 130, 257-263, 1986); and Y. Wu et al. (Eur. J. Pharmacol., 278, 125-132, 1995) using 96-well microtiter plates. The membranes containing the study receptors, flumazenil (radiolabeling at a final concentration of 1 nM) and ascending concentrations of test compounds (in a total volume of 230 µl in 50 mM [pH 7.4] Tris.HCl buffer) were incubated. Simultaneously, the membranes were only incubated with the radiolabeled flumazenil (total binding, 100%) and in the presence of an elevated concentration of unradio-labeled flumazenil (non-specific binding, % estimation of radiolabeled ligand). The reactions started on adding the radiolabeled ligand followed by incubation for 60 minutes at 4° C. At the end of the incubation period, 200 µl of reaction were transferred to a multiscreen plate (Millipore) and filtered using a vacuum manifold and then washed three times with cold test buffer. The multiscreen plates were equipped with a GF/B filter that retained the membranes containing the receptors and the radiolabeled ligand which had been bound to the receptors. After washing, the plates were left till dry. Once dried, scintillation liquid was added and left under stirring overnight. The next day the plates were counted using a Perkin-Elmer Microbeta scintillation counter.

For analysis of the results the percentage of specific binding for every concentration of test compound was calculated as follows:

$$\% \text{ specific binding} = (X-N/T-N) \times 100$$

where,

X: amount of bound ligand for every concentration of compound.

T: total binding, maximum amount bound to the radiolabeled ligand.

N: non-specific binding, amount of radiolabeled ligand bound in a non-specific way irrespective of the receptor used.

Every concentrations of compound were tested in triplicate and their mean values were used to determine the experimental values of % specific binding versus the concentration of compound. Affinity data are expressed as % inhibition at $10^{-5}$ M and $10^{-7}$ M concentrations. The results of these tests are given in Tables 1 and 2.

TABLE 1

Affinity for the $\alpha_1$-subunit of the GABA$_A$ receptor

| Compound | % Inhib $10^{-5}$M | % Inhib $10^{-7}$M |
| --- | --- | --- |
| Example 3 | 98.7 | 55.9 |
| Example 6 | 99.0 | 59.1 |
| Example 7 | 46.1 | 0.9 |
| Example 8 | 97.6 | 25.2 |
| Example 9 | 98.5 | 24.2 |
| Zolpidem | 73.6 | — |

TABLE 2

Affinity for the $\alpha_2$-subunit of the GABA$_A$ receptor

| Compound | % Inhib $10^{-5}$M | % Inhib $10^{-7}$M |
| --- | --- | --- |
| Example 3 | 80.8 | 25.8 |
| Example 6 | 71.6 | 2.0 |
| Example 8 | 88.6 | 11.2 |
| Example 9 | 86.6 | 21.9 |
| Zolpidem | 74.1 | 19.9 | b) In Vivo Determination of Predictive Sedative-Hypnotic Action

The in vivo effects of these compounds were assessed by a predictive sedation-hypnosis test in mice (D. J. Sanger et al., Eur. J. Pharmacol., 313, 35-42, 1996; and G. Griebel et al., Psychopharmacology, 146, 205-213, 1999).

Groups of 5-8 male CD1 mice, weighing 22-26 g at the time of test, were used. The test compounds were administered in single equimolecular intraperitoneal doses, suspended in 0.25% agar with one drop of Tween in a volume of 10 mL/kg. Control animals received the vehicle alone. Using a Smart System (Panlab, S. L., Spain) the traveled distance in cm was recorded for each mouse at 5 min intervals during a period of 30 minutes after dosing. The inhibition percentage traveled distance of treated animals versus control animals (the first 5 min were discarded) was calculated. The results of this test are given in Table 3.

TABLE 3

In vivo determination of sedative-hypnotic activity in mice.

| Compound | % Motor activity inhibition |
| --- | --- |
| Example 3 | 92.03 |
| Example 6 | 93.42 |
| Example 7 | 25.05 |
| Example 8 | 90.16 |
| Example 9 | 92.03 |
| Zolpidem | 91.70 |

Indeed, when a dose-response curve was obtained, the compound of example 3 exhibited in vivo a 2-fold greater potency in inhibiting spontaneous motor activity (ID$_{50}$=1.9 µmol/kg) compared to zolpidem (ID50=4.4 µmol/kg), the prior art compound used as positive control for this assay.

The following non-limiting examples illustrate the scope of the present invention.

Example A

Preparation of the Intermediate Ketoester Compound (III, R=CH₃)

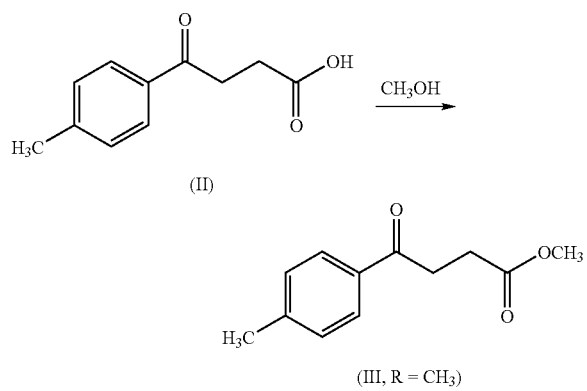

To a solution of (II) (1 eq) in methanol was added dropwise a solution of concentrated $H_2SO_4$ (0.5 eq) in methanol. The mixture was stirred at reflux for 30 minutes. The solvent was removed in vacuo and the residue extracted with dichloromethane/NaOH 1N and with dichloromethane/water. The organic layer was dried over $Na_2SO_4$ and filtered off, and the solvent was removed in vacuo to afford the ketoester (III, R=CH₃).

$^1$H NMR (400 MHz, DMSO-$d_6$): δ 7.77-7.14 (m, 4H, Ar), 3.67 (s, 3H, OCH₃), 2.94 (t, 2H, CH₂CO), 2.44 (t, 2H, CH₂COO), 2.35 (s, 3H, CH₃).
MS (ES) m/z=207 (MH⁺)
HPLC=100%

Example B

Preparation of the Intermediate Bromoketoester Compound (IV, R=CH₃)

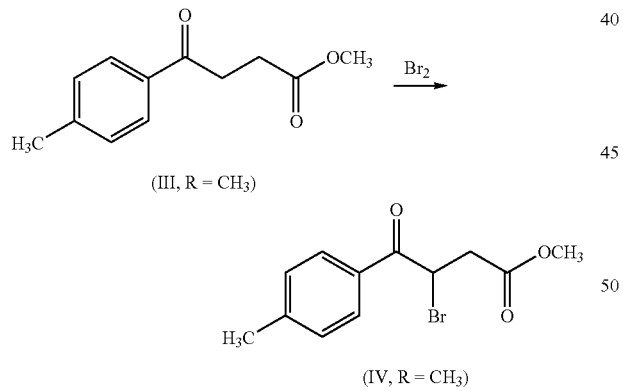

To a solution of (III, R=CH₃) (1 eq) in acetic acid was added dropwise a solution of bromine (2.2 eq) in acetic acid. The mixture was stirred at room temperature for 24 h. The solvent was removed in vacuo and the residue was extracted with dichloromethane/NaOH 1N and with dichloromethane/water. The organic layer was dried over $Na_2SO_4$ and filtered off, and the solvent was removed in vacuo to afford the bromoketoester (IV, R=CH₃).

$^1$H NMR (400 MHz, DMSO-$d_6$): δ 7.90-7.03 (m, 4H, Ar), 5.60 (t, 1H, CHBr), 3.75 (s, 3H, OCH₃), 2.85 (t, 2H, CH₂COO), 2.32 (s, 3H, CH₃).
MS (ES) m/z=285 (M), 287 (M+2H)
HPLC=100%

Example C

Preparation of the Intermediate imidazo[1,2-a]pyridin-3-yl-acetic Acid Ester Compound (VI, R=CH₃)

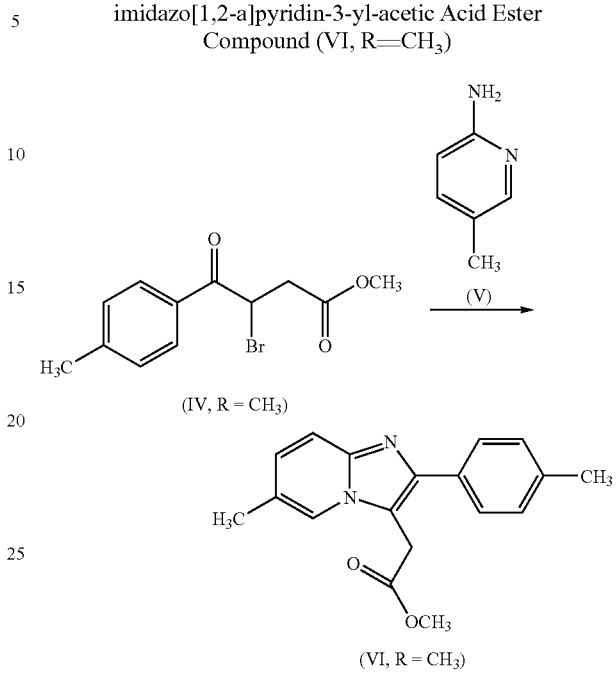

To a solution of (IV R=CH₃) (1 eq) in acetonitrile was added a solution of (V) (1.2 eq) in acetonitrile. The mixture was stirred at reflux for 2 h. The solvent was removed in vacuo and the residue was extracted with dichloromethane/HCl 1N and with dichloromethane/water. The organic layer was dried over $Na_2SO_4$ and filtered off, and the solvent was removed in vacuo to afford the imidazo[1,2-a]pyridin-3-yl-acetic acid ester (VI, R=CH₃).

$^1$H NMR (400 MHz, DMSO-$d_6$): δ 7.80-6.80 (m, 7H, Ar), 3.95 (s, 3H, OCH₃), 3.45 (s, 2H, CH₂), 2.35 (s, 3H, CH₃), 3.32 (s, 3H, CH₃).
MS (ES) m/z=295 (MH⁺)
HPLC=100%

Example D

General Process for Preparing N'-acyl imidazo[1,2-a]pyridin-3-yl-acetic Acid Hydrazides (I, R₂=R₄CO)

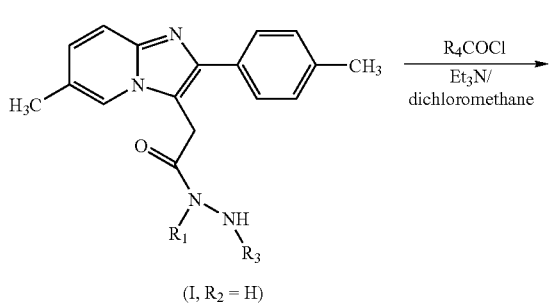

-continued

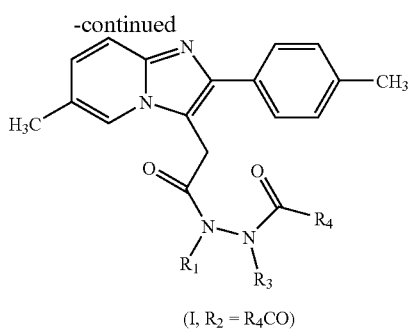

(I, R₂ = R₄CO)

To a solution of (I, R₂=H) (1 eq) in dichloromethane was added a solution of N(C₂H₅)₃ (2 eq) in dichloromethane. To this mixture was added dropwise a solution of R₄COCl (1.2 eq) in dichloromethane. The mixture was stirred at room temperature for 24 h. The solvent was removed in vacuo and the residue was extracted with dichloromethane/NaOH 1 N, with dichloromethane/HCl 1N and with dichloromethane/water. The organic layer was dried over Na₂SO₄ and filtered off, and the solvent was removed in vacuo to afford the N'-acyl imidazo[1,2-a]pyridin-3-yl-acetic acid hydrazides (I, R₂=R₄CO).

Compounds of examples 1 and 2 were prepared according to this process.

Example 1

Thiophene-2-carboxylic acid N'-[2-(6-methyl-2-p-tolyl-imidazo[1,2-a]pyridin-3-yl)-acetyl]-hydrazide

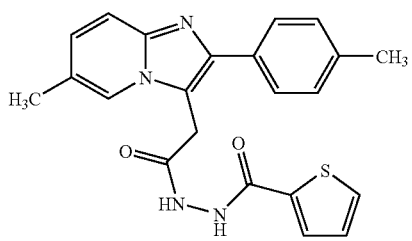

MS (ES) m/z=405 (MH⁺)
HPLC=83%

Example 2

(6-Methyl-2-p-tolyl-imidazo[1,2-a]pyridin-3-yl)-acetic Acid N'-acetyl-hydrazide

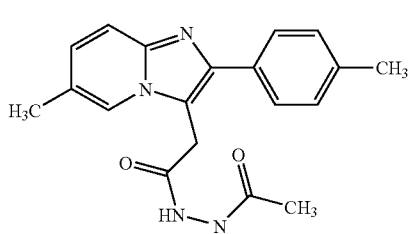

MS (ES) m/z=307 (MH⁺)
HPLC=89%

Example E

General Process for Preparing imidazo[1,2-a]pyridin-3-yl-acetic Acid Hydrazides (I)

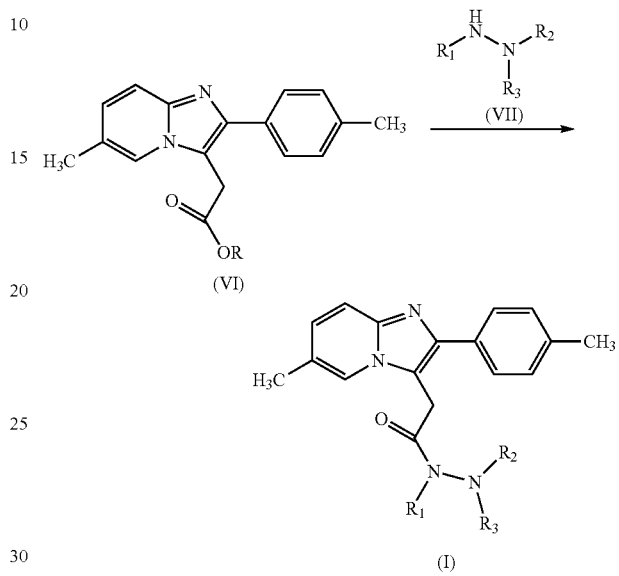

To a solution of (VI) (1 eq) in methanol was added a solution of (substituted) hydrazine (VII) (5 eq) in methanol. The mixture was stirred at reflux for 24 h. The solvent was removed in vacuo and the residue was extracted with dichloromethane/HCl 1N and with dichloromethane/water. The organic layer was dried over Na₂SO₄ and filtered off, and the solvent was removed in vacuo to afford the imidazo[1,2-a]pyridin-3-yl-acetic acid hydrazides (I).

Compounds of examples 3-6 were prepared according to this process.

Example 3

(6-Methyl-2-p-tolyl-imidazo[1,2-a]pyridin-3-yl)-acetic Acid Hydrazide

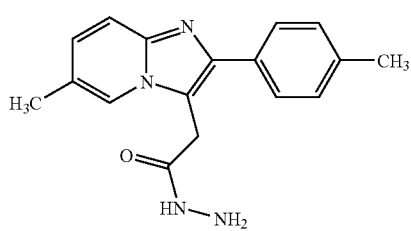

¹H NMR (400 MHz, DMSO-d₆): δ 7.90-7.03 (m, 7H, Ar), 3.28 (s, 2H, CH₂), 2.35 (s, 3H, CH₃), 2.32 (s, 3H, CH₃).
MS (ES) m/z=312 (MH⁺)
HPLC=100%

Example 4

2-(6-Methyl-2-p-tolyl-imidazo[1,2-a]pyridin-3-yl)-N-morpholin-4-yl-acetamide

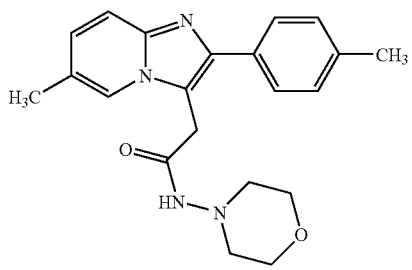

MS (ES) m/z=365 (MH$^+$)
HPLC=100%

Example 5

2-(6-Methyl-2-p-tolyl-imidazo[1,2-a]pyridin-3-yl)-N-[1,2,4]triazol-4-yl-acetamide

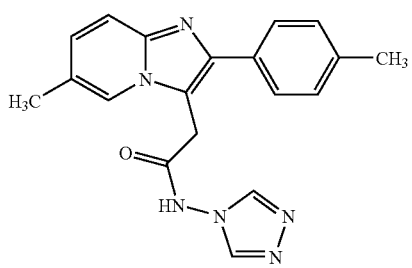

MS (ES) m/z=347 (MH$^+$)
HPLC=100%

Example 6

(6-Methyl-2-p-tolyl-imidazo[1,2-a]pyridin-3-yl)-acetic Acid N-methyl-hydrazide

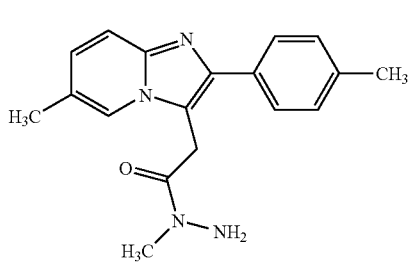

MS (ES) m/z=309 (MH$^+$)
HPLC=87%

Example F

General Process for Preparing alkyl-(or aryl-)iden imidazo[1,2-a]pyridin-3-yl-acetic Acid Hydrazides (I, NR$_2$R$_3$=NCR$_5$R$_6$)

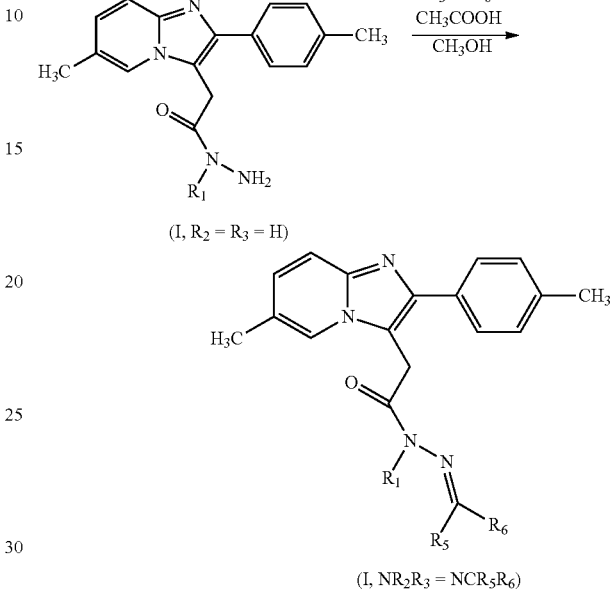

To a solution of (I, R$_2$=R$_3$=H) (1 eq) in methanol was added a solution of R$_5$COR$_6$ (aldehyde or ketone) (5 eq) in methanol. To this mixture were added a few drops of acetic acid. The mixture was stirred at reflux for 3 h. The solvent was removed in vacuo and the residue was extracted with dichloromethane/water. The organic layer was dried over Na$_2$SO$_4$ and filtered off, and the solvent was removed in vacuo to afford the alkyl-(or aryl-)iden imidazo[1,2-a]pyridin-3-yl-acetic acid hydrazides (I, NR$_2$R$_3$=NCR$_5$R$_6$).

Compounds of examples 7-9 were prepared according to this process.

Example 7

(6-Methyl-2-p-tolyl-imidazo[1,2-a]pyridin-3-yl)-acetic Acid (4-chlorobenzylidene)-hydrazide

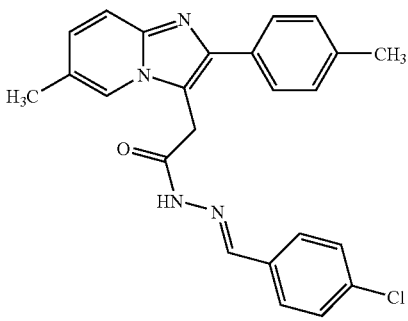

MS (ES) m/z=418 (MH$^+$)
HPLC=89%

Example 8

(6-Methyl-2-p-tolyl-imidazo[1,2-a]pyridin-3-yl)-acetic Acid Ethylidene-hydrazide

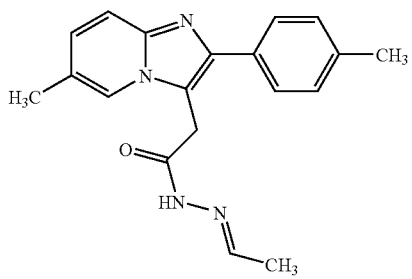

MS (ES) m/z=321 (MH⁺)
HPLC=86%

Example 9

(6-Methyl-2-p-tolyl-imidazo[1,2-a]pyridin-3-yl)-acetic acid isopropylidene-hydrazide

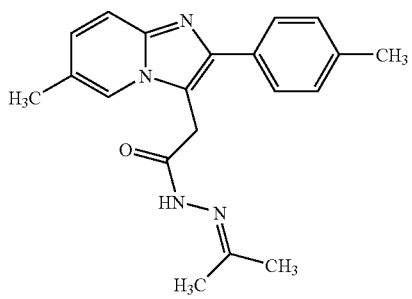

MS (ES) m/z=335 (MH⁺)
HPLC=89%

Example 10

5 mg Tablets

| | |
|---|---|
| Compound of example 3 | 5.0 mg |
| Colloidal silicon dioxide | 0.6 mg |
| Croscarmellose sodium | 12.0 mg |
| Talc | 4.0 mg |
| Magnesium stearate | 1.5 mg |
| Polysorbate 80 | 1.0 mg |
| Lactose | 75.0 mg |
| Hydroxypropyl methylcellulose | 3.0 mg |
| Polyethylene glycol 4000 | 0.5 mg |
| Titanium dioxide E171 | 1.5 mg |
| Microcrystalline cellulose q.s. to | 125.0 mg |

Example 11

10 mg Capsules

| | |
|---|---|
| Compound of example 3 | 10.0 mg |
| Colloidal silicon dioxide | 0.6 mg |
| Crospovidone | 12.0 mg |
| Talc | 4.0 mg |
| Magnesium stearate | 1.5 mg |
| Lauryl sulfate sodium | 1.5 mg |
| Lactose | 77.0 mg |
| Gelatin | 28.5 mg |
| Titanium dioxide E171 | 1.5 mg |
| Indigotin E132 | 0.02 mg |
| Microcrystalline cellulose q.s. to | 155.0 mg |

Example 12

0.5 g Oral Drops

| | |
|---|---|
| Compound of example 3 | 0.5 g |
| Propylene glycol | 10.0 g |
| Glycerin | 5.0 g |
| Saccharin sodium | 0.1 g |
| Polysorbate 80 | 1.0 g |
| Lemon flavor | 0.2 g |
| Ethanol | 25.0 mL |
| Purified water q.s. to | 100.0 mL |

Example 13

2.5 mg Tablets

| | |
|---|---|
| Compound of example 3 | 2.5 mg |
| Colloidal silicon dioxide | 0.6 mg |
| Croscaramellose sodium | 12.0 mg |
| Talc | 4.0 mg |
| Magnesium stearate | 1.5 mg |
| Polysorbate 80 | 1.0 mg |
| Lactose | 75.0 mg |
| Hydroxypropyl methylcellulose | 3.0 mg |
| Polyethylene glycol 4000 | 0.5 mg |
| Titanium dioxide E171 | 1.5 mg |
| Microcrystalline cellulose q.s. to | 125.0 mg |

Example 14

5 mg Capsules

| | |
|---|---|
| Compound of example 3 | 5.0 mg |
| Colloidal silicon dioxide | 0.6 mg |
| Crospovidone | 12.0 mg |
| Talc | 4.0 mg |
| Magnesium stearate | 1.5 mg |
| Lauryl sulfate sodium | 1.5 mg |
| Lactose | 77.0 mg |

-continued

| | |
|---|---|
| Gelatin | 28.5 mg |
| Titanium dioxide E171 | 1.5 mg |
| Indigotin E132 | 0.02 mg |
| Microcrystalline q.s. to | 155.0 mg |

Example 15

0.25 g Oral Drops

| | |
|---|---|
| Compound of example 3 | 0.25 g |
| Propylene glycol | 10.0 g |
| Glycerin | 5.0 g |
| Saccharin sodium | 0.1 g |
| Polysorbate 80 | 1.0 g |
| Lemon flavor | 0.2 g |
| Ethanol | 25.0 mL |
| Purified q.s. to | 100.0 mL |

The invention claimed is:

1. An imidazo[1,2-a]pyridin-3-yl-acetic acid hydrazide compound of formula (I):

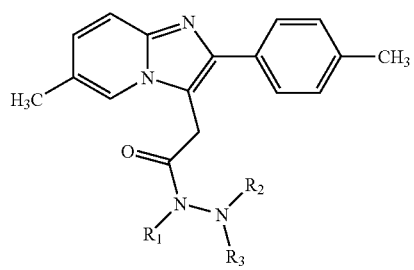

(I)

wherein
R₁ is selected from the group consisting of hydrogen, linear or branched alkyl($C_1$-$C_6$), alkenyl($C_2$-$C_6$), alkynyl($C_2$-$C_6$) and cycloalkyl($C_3$-$C_6$);
R₂ and R₃ are independently selected from the group consisting of hydrogen, linear or branched alkyl($C_1$-$C_6$), alkenyl($C_2$-$C_6$), alkynyl($C_2$-$C_6$), cycloalkyl($C_3$-$C_6$) and R₄CO, or both R₂ and R₃ can form, together with the nitrogen atom to which they are attached, a 5-6 membered heterocyclic ring optionally substituted, or a NCR₅R₆ group;
R₄ is selected from the group consisting of linear or branched alkyl($C_1$-$C_6$), cycloalkyl($C_3$-$C_6$), aryl optionally substituted and heteroaryl optionally substituted;
R₅ is selected from the group consisting of hydrogen, linear or branched alkyl($C_1$-$C_6$), cycloalkyl($C_3$-$C_6$) and aryl optionally substituted;
R₆ is selected from the group consisting of linear or branched alkyl($C_1$-$C_6$), cycloalkyl($C_3$-$C_6$) and aryl optionally substituted;
or both R₅ and R₆ can form, together with the carbon atom to which they are attached, a 5-6 membered ring optionally substituted; and
pharmaceutically acceptable salts, tautomers, and stereoisomers thereof.

2. The compound according to claim 1, wherein R₁ is selected from the group consisting of hydrogen and methyl; and R₂ and R₃ are independently selected from the group consisting of hydrogen, acetyl and 2-thiophenecarbonyl, or both R₂ and R₃ form, together with the nitrogen atom to which they are attached, a heterocycle selected from 1-morpholinyl and 1,2,4-triazin-4-yl, or a NCR₅R₆ group selected from ethylideneamino, isopropylideneamino and 4-chlorobenzylideneamino.

3. The compound according to claim 2, wherein said compound is selected from the group consisting of:

Thiophene-2-carboxylic acid N'-[2-(6-methyl-2-p-tolyl-imidazo [1,2-a]pyridin-3-yl)-acetyl]-hydrazide;

(6-Methyl-2-p-tolyl-imidazo[1,2-a]pyridin-3-yl)-acetic acid N'-acetyl-hydrazide;

(6-Methyl-2-p-tolyl-imidazo[1,2-a]pyridin-3-yl)-acetic acid hydrazide;

2-(6-Methyl-2-p-tolyl-imidazo[1,2-a]pyridin-3-yl)-N-morpholin -4-yl-acetamide;

2-(6-Methyl-2-p-tolyl-imidazo[1,2-a]pyridin-3-yl)-N-[1,2,4]triazol-4-yl-acetamide;

(6-Methyl-2-p-tolyl-imidazo[1,2-a]pyridin-3-yl)-acetic acid N-methyl-hydrazide;

(6-Methyl-2-p-tolyl-imidazo[1,2-a]pyridin-3-yl)-acetic acid (4-chlorobenzylidene)-hydrazide;

(6-Methyl-2-p-tolyl-imidazo[1,2-a]pyridin-3-yl)-acetic acid ethylidene-hydrazide; and (6-Methyl-2-p-tolyl-imidazo[1,2-a]pyridin-3-yl)-acetic acid isopropylidene-hydrazide.

4. A process for preparing a compound of formula (I) as defined in claim 1, comprising reacting an intermediate compound of formula (VI):

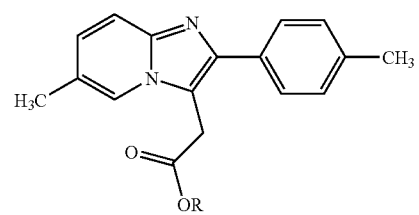

(VI)

wherein R is a linear or branched alkyl($C_1$-$C_6$) or a phenylalkyl($C_1$-$C_3$) group with the appropriate hydrazine compound of formula (VII):

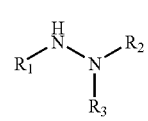

(VII)

wherein R₁, R₂ and R₃ are as defined for (I), and alternatively, treating the resulting compounds in the form of free base, with an appropriate acid to form a pharmaceutically acceptable salt thereof.

5. The process according to claim 4, wherein in a further step a compound of formula (IV)

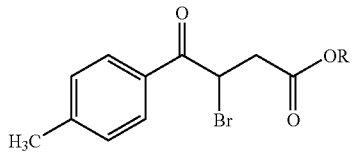
(IV)

wherein R is as defined in (VI) is reacted with 2-amino-5-methylpyridine (V) to give the compound (VI).

6. The process according to claim 4, comprising utilizing the intermediate compound of formula (VI) wherein R is methyl.

7. The process according to claim 5 comprising utilizing the intermediate compound of formula (IV) wherein R is methyl.

8. A process for preparing a compound of formula (I) as defined in claim 1, wherein $R_2$ is $R_4CO$, comprising reacting the compound (I, $R_2$=H) with the corresponding acid chloride $R_4COCl$, wherein $R_4$ is as defined above.

9. A process for preparing a compound of formula (I) as defined in claim 1, when $NR_2R_3$ is $NCR_5R_6$, comprising reacting the compound (I, $R_2$=$R_3$=H) with the corresponding aldehyde or ketone $R_5COR_6$, wherein $R_5$ and $R_6$ are as defined above.

10. A pharmaceutical composition comprising a therapeutically effective amount of a compound as defined in claim 1, together with appropriate amounts of pharmaceutical excipients or carriers.

* * * * *